(12) United States Patent
Smith

(10) Patent No.: US 9,226,770 B2
(45) Date of Patent: Jan. 5, 2016

(54) OPTICAL PENETRATING ADAPTER FOR SURGICAL PORTAL

(71) Applicant: Covidien LP, Mansfield, MA (US)

(72) Inventor: Robert C. Smith, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/893,711

(22) Filed: May 14, 2013

(65) Prior Publication Data

US 2013/0289601 A1    Oct. 31, 2013

Related U.S. Application Data

(60) Continuation of application No. 13/273,657, filed on Oct. 14, 2011, now Pat. No. 8,475,486, which is a division of application No. 11/046,256, filed on Jan. 28, 2005, now Pat. No. 8,070,767.

(51) Int. Cl.
| | |
|---|---|
| *A61B 17/34* | (2006.01) |
| *A61B 1/00* | (2006.01) |
| *A61B 1/313* | (2006.01) |
| *A61B 19/00* | (2006.01) |
| *A61B 17/00* | (2006.01) |

(52) U.S. Cl.
CPC ......... *A61B 17/3417* (2013.01); *A61B 1/00135* (2013.01); *A61B 1/3132* (2013.01); *A61B 19/5212* (2013.01); *A61B 2017/00473* (2013.01); *A61B 2017/3456* (2013.01)

(58) Field of Classification Search
CPC .............. A61B 17/3417; A61B 17/34; A61B 17/3421; A61B 17/3462; A61B 2017/3454; A61B 2017/3456; A61B 17/3458
USPC .......... 606/167, 184, 185, 170, 108; 600/174, 600/175, 101, 114, 136, 129, 160, 121, 171, 600/184; 604/164.01, 164.03, 164.05, 604/164.06, 167.01–167.04, 170.01, 604/170.03, 272, 158, 166.04, 164.08, 264; 30/358–368, 346.57, 48, 162; 83/803, 83/792, 856–858, 651, 660, 667–669; 408/189–191, 194–196
See application file for complete search history.

(56) References Cited

U.S. PATENT DOCUMENTS

| | | |
|---|---|---|
| 2,566,738 A | 9/1951 | Mitchell |
| 3,760,810 A | 9/1973 | Van Hoorn |
| 4,878,485 A | 11/1989 | Adair |
| 5,169,397 A | 12/1992 | Sakashita et al. |
| 5,226,690 A | 7/1993 | Ianniruberto et al. |
| 5,250,068 A | 10/1993 | Ideguchi et al. |

(Continued)

OTHER PUBLICATIONS

European Search Report EP06001607 dated Mar. 13, 2006.

(Continued)

*Primary Examiner* — Jocelin Tanner

(57) ABSTRACT

An optical penetrating adapter for mounting to a surgical portal to permit visualization through the surgical portal includes an adapter member defining a longitudinal axis and having a transparent window adapted to penetrate tissue and to permit visualization therethrough and means for coupling the adapter member to the surgical portal. The transparent window may have various shapes and configurations adapted to penetrate, dissect, resect or separate tissue in a non traumatic manner. Alternatively, the transparent window may incorporate structure such as cutting edges blades, points, etc to pierce, cut or incise tissue.

15 Claims, 7 Drawing Sheets

(56) References Cited

U.S. PATENT DOCUMENTS

| | | |
|---|---|---|
| 5,256,149 A | 10/1993 | Banik et al. |
| 5,271,380 A | 12/1993 | Riek et al. |
| 5,290,276 A | 3/1994 | Sewell, Jr. |
| 5,334,150 A | 8/1994 | Kaali |
| 5,354,302 A | 10/1994 | Ko |
| 5,370,640 A | 12/1994 | Kolff |
| 5,376,076 A | 12/1994 | Kaali |
| 5,380,291 A | 1/1995 | Kaali |
| 5,385,572 A | 1/1995 | Nobles et al. |
| 5,408,992 A | 4/1995 | Hamlin et al. |
| 5,431,151 A | 7/1995 | Riek et al. |
| 5,441,041 A | 8/1995 | Sauer et al. |
| 5,445,142 A | 8/1995 | Hassler, Jr. |
| 5,467,762 A | 11/1995 | Sauer et al. |
| 5,551,947 A | 9/1996 | Kaali |
| 5,563,696 A | 10/1996 | Nobles et al. |
| 5,569,160 A | 10/1996 | Sauer et al. |
| 5,569,291 A | 10/1996 | Privitera et al. |
| 5,569,292 A | 10/1996 | Scwemberger |
| 5,571,133 A | 11/1996 | Yoon |
| 5,591,186 A | 1/1997 | Wurster et al. |
| 5,591,191 A | 1/1997 | Kieturakis |
| 5,591,192 A | 1/1997 | Privitera et al. |
| 5,609,562 A | 3/1997 | Kaali |
| 5,632,717 A | 5/1997 | Yoon |
| 5,658,236 A | 8/1997 | Sauer et al. |
| 5,658,306 A | 8/1997 | Kieturakis et al. |
| 5,662,613 A | 9/1997 | Astarita |
| 5,662,673 A | 9/1997 | Kieturakis |
| 5,674,184 A | 10/1997 | Hassler, Jr. |
| 5,681,323 A | 10/1997 | Arick |
| 5,685,820 A | 11/1997 | Riek et al. |
| 5,707,382 A | 1/1998 | Sierocuk et al. |
| 5,720,761 A | 2/1998 | Kaali |
| 5,738,628 A | 4/1998 | Sierocuk |
| 5,797,944 A | 8/1998 | Nobles et al. |
| 5,807,317 A | 9/1998 | Krech, Jr. |
| 5,817,061 A * | 10/1998 | Goodwin et al. ........ 604/164.03 |
| 5,843,115 A | 12/1998 | Morejon |
| 5,857,999 A | 1/1999 | Quick et al. |
| 5,860,996 A | 1/1999 | Urban et al. |
| 5,873,889 A | 2/1999 | Chin |
| 5,980,549 A | 11/1999 | Chin |
| RE36,434 E | 12/1999 | Hamlin et al. |
| 6,007,481 A | 12/1999 | Riek et al. |
| 6,106,539 A * | 8/2000 | Fortier ......................... 606/185 |
| 6,176,824 B1 | 1/2001 | Davis |
| 6,203,557 B1 | 3/2001 | Chin |
| 6,206,823 B1 | 3/2001 | Kolata et al. |
| 6,228,059 B1 | 5/2001 | Astarita |
| 6,478,806 B2 | 11/2002 | McFarlane |
| 6,685,630 B2 | 2/2004 | Sauer et al. |
| 6,692,467 B2 | 2/2004 | McFarlane |
| 6,695,816 B2 | 2/2004 | Cassidy, Jr. |
| 6,830,578 B2 | 12/2004 | O'Heeron |
| 2001/0029388 A1 | 10/2001 | Kieturakis et al. |
| 2002/0099289 A1 | 7/2002 | Crowley |
| 2002/0115918 A1 | 8/2002 | Crowley |
| 2002/0143236 A1 | 10/2002 | Sauer et al. |
| 2002/0188201 A1 | 12/2002 | Crowley |
| 2003/0033304 A1* | 2/2003 | Uesaka ......................... 707/10 |
| 2003/0187471 A1 | 10/2003 | Cooper |
| 2004/0015182 A1 | 1/2004 | Kieturakis et al. |
| 2005/0107816 A1* | 5/2005 | Pingleton et al. ............. 606/185 |

OTHER PUBLICATIONS

Canadian Office Action dated May 16, 2013.

* cited by examiner

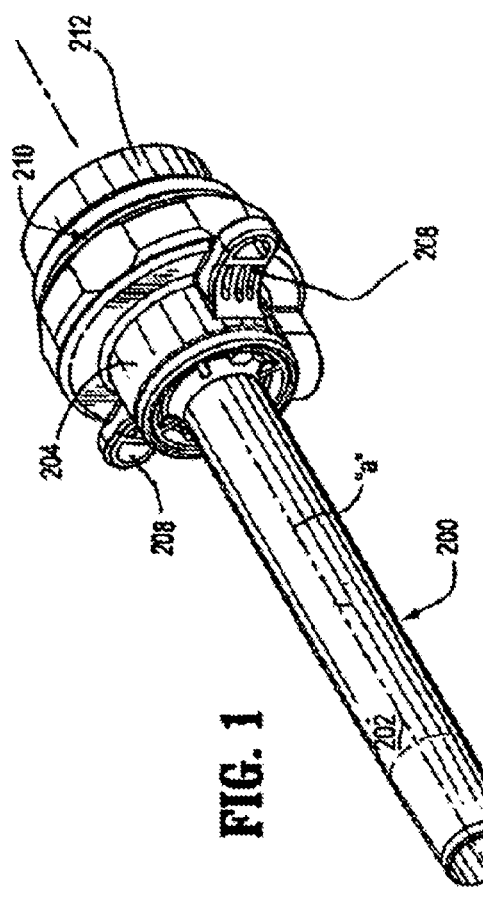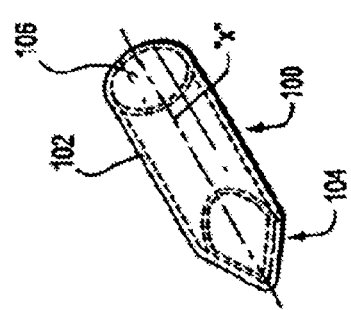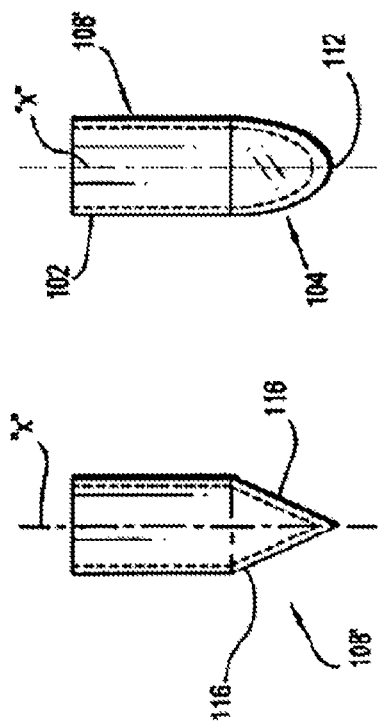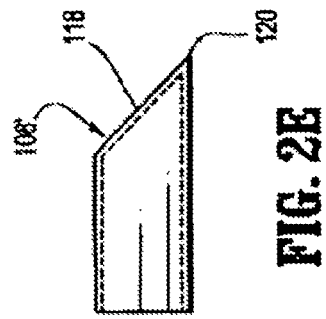

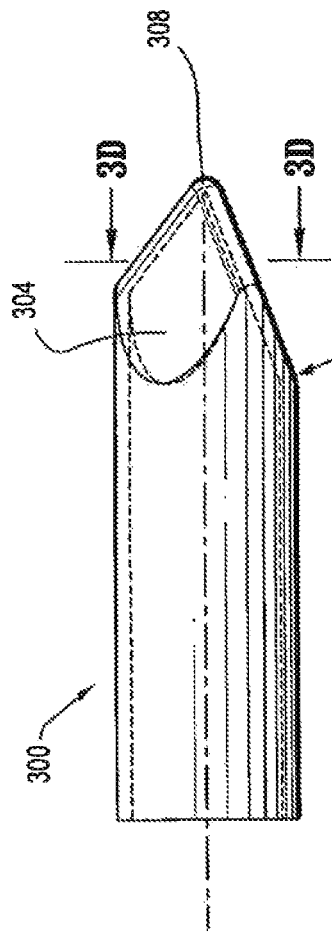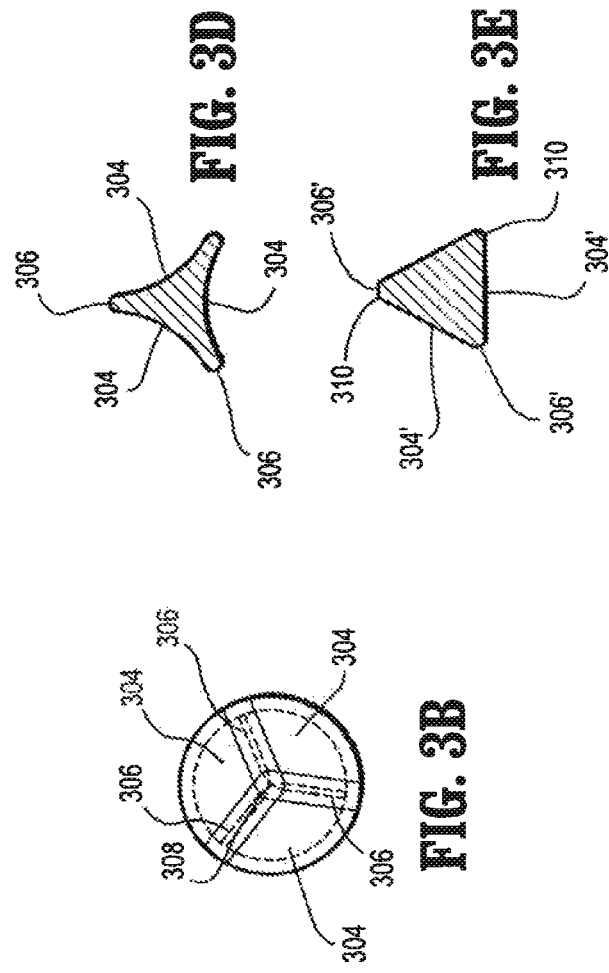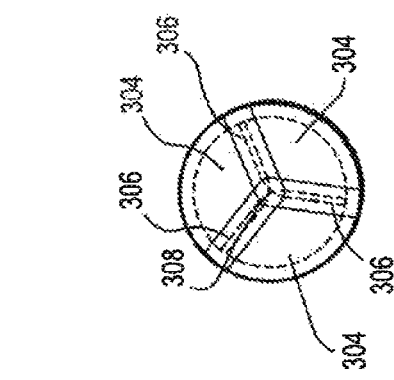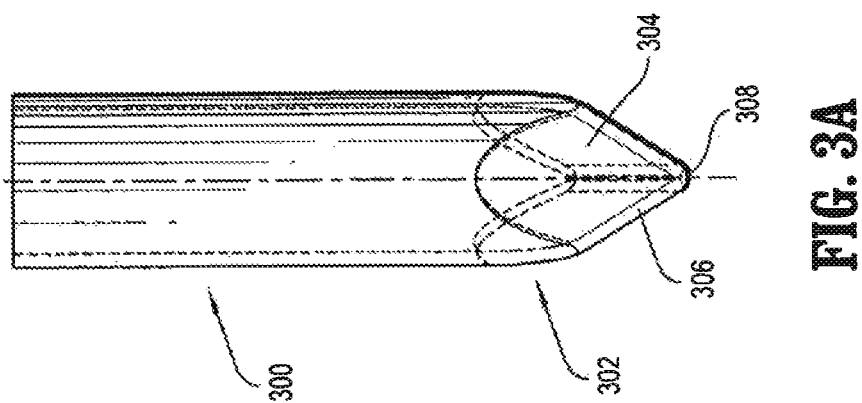

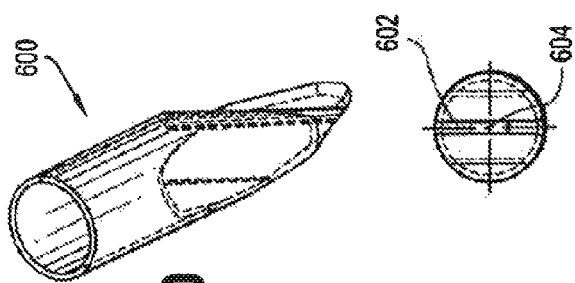
FIG. 6D
FIG. 6E
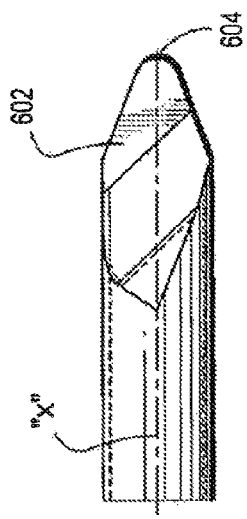
FIG. 6C
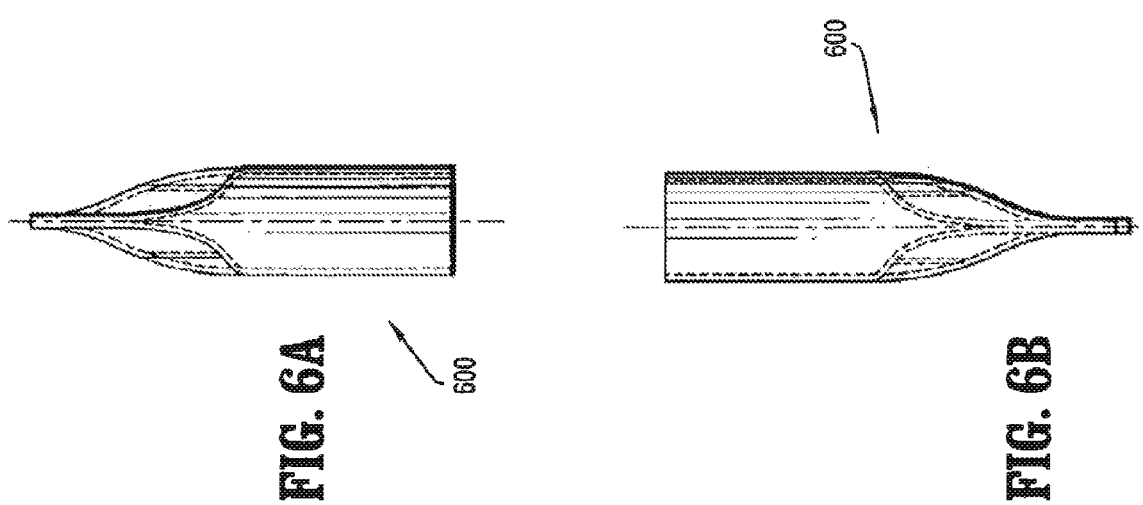
FIG. 6A
FIG. 6B

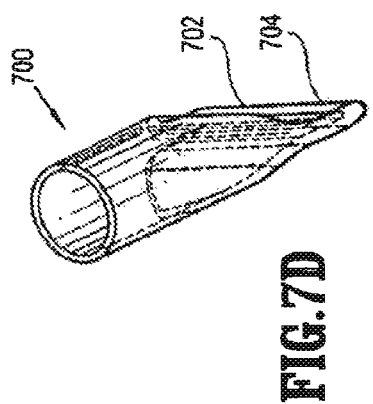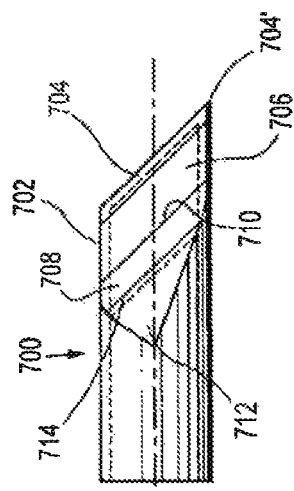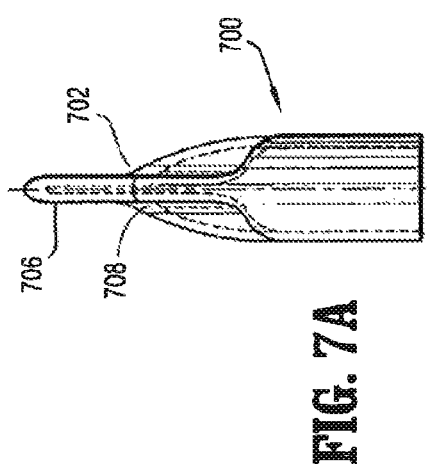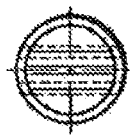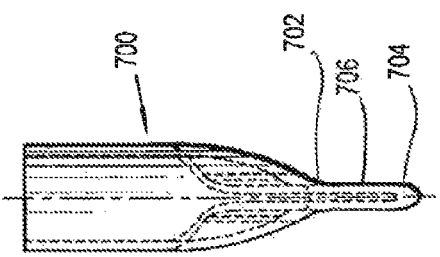
FIG. 7D
FIG. 7C
FIG. 7A
FIG. 7E
FIG. 7B

OPTICAL PENETRATING ADAPTER FOR SURGICAL PORTAL

CROSS-REFERENCE TO RELATED APPLICATIONS

This application is a continuation U.S. patent application Ser. No. 13/273,657, filed on Oct. 14, 2011, which is a divisional of U.S. patent application Ser. No. 11/046,256, filed on Jan. 28, 2005, now U.S. Pat. No. 8,070,767, the entire content of each of the applications identified above being incorporated by reference herein.

BACKGROUND

1. Technical Field

The present disclosure relates to an apparatus for penetrating body tissue during minimally invasive surgical procedures, such as endoscopic or laparoscopic procedures. More particularly, the present disclosure relates to an optical penetrating adapter for mounting to an endoscopic portal for providing penetrating capabilities to the portal while also permitting visual observation during penetration of the peritoneum or other body tissue.

2. Background of the Related Art

Minimally invasive surgical procedures, including endoscopic and laparoscopic procedures, permit surgery to be performed on organs, tissue and vessels far removed from an opening within the tissue. Laparoscopic procedures are performed in the interior of the abdomen through a small incision such as, for example, a narrow endoscopic tube or cannula inserted through a small entrance incision in the skin. Typically, after the abdominal cavity is insufflated, a trocar is used to puncture the cavity wall, i.e., the peritoneal lining, to create a pathway to the underlying surgical site. Generally, the trocar includes a stylet or obturator having a sharp tip for penetrating the body cavity, which is positioned coaxially within an outer cannula. The stylet is removed, leaving the outer cannula in place for reception of instrumentation utilized to perform the surgical procedure. An example of a known trocar is described in commonly assigned U.S. Pat. No. 6,319,266 to Stellon, which issued Nov. 21, 2001, the contents of which are incorporated herein in its entirety by reference. However, with known trocars, advancement of the stylet through tissue is typically performed blind, i.e., without visualization of the tissue being entered.

SUMMARY

Accordingly, the present disclosure is directed to further improvements in accessing tissue during endoscopic or laparoscopic surgical procedures. In particular, the present disclosure provides a transparent penetrating adapter adaptable to a conventional endoscopic portal to permit direct visualization of body tissue during penetration of the body cavity. Moreover, the transparent penetrating adapter may be mounted to a conventional cannula to provide penetrating capabilities to the cannula while providing an optical window for a viewing device positioned in the cannula during entry into the body cavity.

Generally, the present disclosure is directed to a method for the abdominal cavity, including the steps of providing a penetrating end member adapted to pass through tissue, mounting the penetrating end member to a surgical portal and advancing the penetrating end member through the abdominal wall to permit the surgical portal to access an underlying surgical site.

The present disclosure is also directed to a method for providing visualized entry into the abdominal cavity, including the steps of providing an optical penetrating adapter, coupling the optical penetrating adapter to a surgical portal, positioning a viewing device within the surgical portal and advancing the surgical portal through the abdominal wall while viewing with the viewing device the underlying tissue through the optical penetrating adapter.

In an alternate embodiment, the present disclosure is directed to an optical penetrating system including a surgical portal having at least one seal for maintaining insufflation pressure in the abdominal cavity, an adapter member defining a longitudinal axis and having a transparent window adapted to penetrate tissue and to permit visualization therethrough, and means for coupling the adapter member to the surgical portal. The transparent window may have various shapes and configurations adapted to penetrate, dissect, resect or separate tissue in a non traumatic manner. Alternatively, the transparent window may incorporate structure such as cutting edges blades, points, etc to pierce, cut or incise tissue.

A kit incorporating at least one or a plurality of different optical penetrating adapters with or without a cannula and/or endoscope is also contemplated.

BRIEF DESCRIPTION OF THE DRAWINGS

Preferred embodiments of the present disclosure are described hereinbelow with references to the drawings, wherein:

FIG. 1 is a perspective view of the optical penetrating adapter in accordance with the principles of the present disclosure and shown in a disassembled condition relative to a cannula assembly;

FIG. 2A is a side plan view of the optical penetrating adapter mounted about the cannula sleeve of the cannula assembly in accordance with the embodiment of FIG. 1;

FIG. 2B is a side plan view of the optical penetrating adapter mounted within the cannula sleeve of the cannula assembly in accordance with an alternate embodiment of the present disclosure;

FIG. 2C is a top plan view of the optical penetrating adapter in accordance with the embodiment of FIGS. 1-2A;

FIG. 2D is a top plan view of an alternate embodiment of the optical penetrating adapter of FIGS. 1-2A;

FIG. 2E is a side plan view of the optical penetrating adapter in accordance with the embodiment of FIG. 2D;

FIG. 3A is a top plan view of an alternate embodiment of the optical penetrating adapter of the present disclosure;

FIG. 3B is an axial view of the optical penetrating adapter in accordance with the embodiment of FIG. 3A;

FIG. 3C is a side plan view of the optical penetrating adapter in accordance with the embodiment of FIGS. 3A-3B;

FIG. 3D is a cross-sectional view taken along the lines 3D-3D of FIG. 3C illustrating the concave surfaces of the optical penetrating adapter in accordance with the embodiment of FIGS. 3A-3C;

FIG. 3E is a cross-sectional view similar to the view of FIG. 3D illustrating an alternate embodiment of the optical penetrating adapter having planar surfaces;

FIG. 6A is a top plan view of another alternate embodiment of the optical penetrating adapter of the present disclosure;

FIG. 6B is a bottom plan view of the optical penetrating adapter in accordance with the embodiment of FIG. 6A;

FIG. 6C is a side plan view of the optical penetrating adapter in accordance with the embodiment of FIGS. 6A-6B;

FIG. 6D is a perspective view of the optical penetrating adapter in accordance with the embodiment of FIGS. 6A-6C;

FIG. 6E is an axial view of the optical penetrating adapter in accordance with the embodiment of FIGS. 6A-6D:

FIG. 7A is a top plan view of another alternate embodiment of the optical penetrating adapter of the present disclosure;

FIG. 7B is a bottom plan view of the optical penetrating adapter in accordance with the embodiment of FIG. 7A;

FIG. 7C is a side plan view of the optical penetrating adapter in accordance with the embodiment of FIGS. 7A-7B;

FIG. 7D is a perspective view of the optical penetrating adapter in accordance with the embodiment of FIGS. 7A-7C; and FIG. 7E is an axial view of the optical penetrating adapter in accordance with the embodiment of FIGS. 7A-7D.

DETAIL DESCRIPTION OF PREFERRED EMBODIMENTS

Figure 4B:
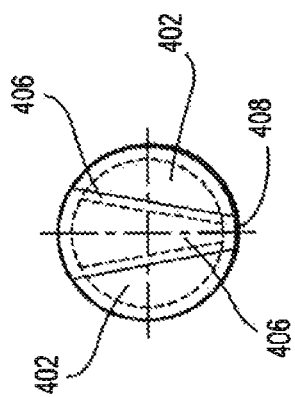
FIG. 4B is an axial view of the optical penetrating adapter in accordance with the embodiment of FIG. 4A.

Referring now to the drawings, in which like reference numerals identify identical or substantially similar parts throughout the several views, FIG. 1 illustrates the optical penetrating adapter 100 of the present disclosure with an access device or portal such as cannula or trocar assembly 200. Cannula assembly 200 may be any conventional cannula suitable for the intended purpose of accessing a body cavity and typically defines a passageway permitting introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which may be blunt, a non-bladed, or a sharp pointed instrument positionable within the passageway of the cannula assembly 200. In a conventional procedure, the obturator assembly is utilized to penetrate the abdominal wall or introduce the cannula assembly 200 through the abdominal wall, and then subsequently is removed from the cannula assembly to permit introduction of the surgical instrumentation utilized to perform the procedure through the passageway.

Cannula assembly 200 includes cannula sleeve 202 and cannula housing 204 mounted to an end of the sleeve 202. Cannula sleeve 202 defines a longitudinal axis "a" extending along the length of the sleeve 202. Sleeve 202 further defines an internal longitudinal passage 206 dimensioned to permit passage of surgical instrumentation. Sleeve 202 may be formed of stainless steel or other rigid materials such as a polymeric material or the like. Sleeve 202 may be clear or opaque. The diameter of sleeve 202 may vary, but typically ranges from about 4.5 to about 15 mm for use with the seal assembly 210 of the present disclosure.

Cannula housing 204 may include several components connected to each other through conventional means or alternatively may be a single housing component. Cannula housing 204 further includes diametrically opposed housing grips 208 dimensioned and arranged for gripping engagement by the fingers of the user. Such grips may include apertures for suture-anchoring the cannula assembly 200 to the body. Cannula housing 204 may be attached to cannula sleeve 202 by any suitable means or may be integrally formed with cannula sleeve 202. Cannula housing 204 may further include an internal zero closure valve which is adapted to close in the absence of a surgical instrument and/or in response to the pressurized environment of the insufflation gases present in the abdominal cavity. One suitable zero closure valve contemplated for use with cannula housing 204 is a duck bill valve, flapper valve, or the like.

Cannula housing 204 may also include seal assembly 210 which is preferably releasably connected to the proximal end of cannula housing 204. Seal assembly 210 includes seal housing 212 and an internal seal (not shown) disposed within seal housing. The internal seal is preferably adapted to form a substantial fluid tight seal about an instrument inserted through the seal. One suitable internal seal is a flat disc-shaped valve, balloon valve, etc. . . . The internal seal may comprise a flat disc-shaped, conical, or hourglass-shaped member including a fabric material molded with an elastomer. The seals disclosed in certain embodiments of commonly assigned U.S. Pat. No. 6,482,181, the entire disclosure of which is hereby incorporated by reference, may be used. Seals disclosed in certain embodiments of commonly assigned U.S. Patent Application No. 2004/0066008A1, filed Oct. 4, 2002 the entire disclosure of which is hereby incorporated by reference herein, may be used. In a further alternative, the internal seal is preferably a fabric seal and is desirably arranged so as to have a constriction. For example, the valve may have the general shape of an hourglass. The fabric can be a woven material, a braided material, or a knitted material. The type of material is selected to provide a desired expansiveness. For example, a braid of varying end count and angle may be selected. A preferred material is a synthetic material such as nylon, Kevlar (Trademark of E.I. DuPont de Nemours and Company) or any other material that will expand and compress about an instrument inserted therethrough. The selected material desirably minimizes or prevents the formation of gaps when the instrument is introduced into the seal. The material of the seal may be porous or impermeable to the insufflation gas. If porous, the seal may include a coating of a material which is impermeable to the insufflation gas or at least a portion of the valve may be coated. In addition, the fabric may be coated on its interior with urethane, silicon or other flexible lubricious materials to facilitate passage of an instrument through the seal. In certain embodiments, the fabric is twisted about the axis "a" so as to form a constriction or closed portion. The fabric is desirably constructed of a material and/or arranged so that the fabric forms a constriction or closure. The seal may also be molded so as to have a constriction or may be knitted, braided or woven so as to have a constriction. Other arrangements for the seal are also envisioned.

Referring now to FIG. 1 and FIG. 2A, optical penetrating adapter 100 of the present disclosure will be discussed. Optical penetrating adapter 100 is contemplated for mounting to cannula sleeve 202 to provide cannula assembly 200 with penetrating capabilities thus obviating the need for a separate obturator introduced within the cannula sleeve 202. Optical penetrating adapter 100 when mounted to cannula assembly 200 is particularly suitable for use with a viewing device such as an endoscope or laparoscope introduced within cannula sleeve 202. In this capacity, optical penetrating adapter 100 serves as a window for the endoscope to permit direct visualization of body tissue during penetration of the peritoneal cavity or other tissue portions. Optical penetrating adapter 100 is dimensioned to pass through body tissue and may incorporate structure to separate, retract, dissect, cut, puncture, or pierce the body tissue. Such structure is inclusive of cutting edges, blades, points, etc.

Optical penetrating adapter 100 includes proximal mounting section 102 and distal penetrating section 104, and defines adapter axis "x". Proximal mounting section 102 is generally cylindrical in configuration defining internal bore 106 which receives the distal end of cannula sleeve 202. In a preferred embodiment, mounting section 102 is dimensioned to engage cannula sleeve 202 and form a frictional relationship therewith so as to mount optical penetrating adapter 100 to cannula assembly 200 as shown in FIG. 2A. Alternatively, as depicted in FIG. 2B, proximal mounting section 102 may be dimensioned to be coaxially positioned within longitudinal passage 206 of cannula sleeve 202 and secured within the cannula sleeve 202 through a frictional relationship or the like. Other means for mounting optical penetrating adapter 100 to cannula sleeve 202 are also envisioned including a bayonet coupling, snap fit, tongue and groove mechanism, etc. The proximal mounting section 102 and cannula sleeve 202 are desirably arranged so that the outer surface of the optical penetrating adapter 100 is flush with the outer surface of the cannula sleeve 202.

Optical penetrating adapter 100 may comprise a polymeric material and be fabricated via known injection molding techniques. Alternatively, optical penetrating adapter 100 may comprise an optical glass. The optical penetrating adapter 100 may be monolithically formed or the proximal mounting section 102 may be a separate component assembled with the distal penetrating section 104.

Distal penetrating section 104 defines transparent window 108 which permits visualization along the adapter axis "x" of cannula sleeve 202 and, desirably, locations offset relative to the adapter axis "x". The term "transparent" is to be interpreted as having the ability to permit the passage of light with or without clear imaging capabilities. Moreover, the transparent material includes any transparent or translucent material or any material which is not opaque to visible light or other radiation utilized for imaging. It is also to be appreciated that only a portion of transparent window 108 needs to be transparent. Furthermore, a portion of optical penetrating adapter 100 or the entire adapter may be translucent or transparent.

Transparent window 108 is generally tapered in configuration, e.g., bulbous or conically-shaped, to facilitate passage through body tissue. In one preferred embodiment, transparent window 108 includes single arcuate surface 110 defining arcuate penetrating end face 112. Penetrating end face 112 is generally arranged at an oblique angle "b" relative to the adapter axis "x" and extends to remote penetrating tip or apex 114. Angle "b" is measured at a central plane passing through axis "x" and may range from about 30° to about 60° and is preferably about 45° relative to adapter axis "x". Penetrating tip 114 may be pointed; however, in the preferred embodiment, penetrating tip 114 is rounded or arcuate as shown. The rounded configuration of penetrating tip 114 prevents undesired piercing or cutting of tissue during entry of penetrating end face 112. Penetrating tip 114 is radially displaced relative to adapter axis "x". Penetrating tip 114 presents a reduced profile to facilitate initial insertion within a narrow incision or opening in tissue. The gradual taper of arcuate surface 110 extends outwardly in directions lateral to axis "x" as well as the vertical direction and provides gradual separation, dissection, and/or retraction of tissue during entry of optical penetrating adapter 100 within the tissue.

In an alternative embodiment, as shown in FIGS. 2D and 2E, transparent window 108' may include a pair of intersecting surfaces 116 in lieu of single arcuate surface 110. Intersecting surfaces 116 are substantially planar but may be concave or convex in configuration. Intersecting surfaces 116 may define an end face edge 118 along the line of intersection of the faces 116. Edge 118 is preferably centered with respect to the longitudinal axis. Thus, during visualization, edge 118 may be seen as a thin line through the viewing field, so as not to substantially obstruct viewing of the body tissue through intersecting surfaces 116. In this embodiment, penetrating tip 120 is pointed which may facilitate piercing or cutting of tissue. Similarly, end face edge 118 may be sharpened to incise the tissue during entry of the adapter. Alternatively, the edges of the transparent window 108' my be curved and more blunt.

FIGS. 3A-3D illustrate an alternate embodiment of the optical penetrating adapter of the present disclosure. Optical penetrating adapter 300 includes penetrating section 302 which is generally pyramidal in configuration, i.e., having at least three primary surfaces 304 arranged to define the tapered optical window shown. Adjacent primary surfaces 304 are connected by auxiliary surfaces 306. Primary and auxiliary surfaces 304, 306 extend to apex or penetrating end face 308 which is preferably rounded, arcuate or blunted. Apex 308 is in general alignment with the adapter axis "x" of optical penetrating adapter 300. Primary surfaces 304 may be concave as shown in FIG. 3D or may be substantially planar primary surfaces 304' as shown in FIG. 3E. Auxiliary surfaces 306 may be generally convex (FIG. 3D) or generally planar 306' in configuration as shown in the embodiment of FIG. 3E. As appreciated, in the embodiment of FIG. 3D, penetrating section 302 is devoid of any sharp edges, due in part to the presence of convex auxiliary surfaces 306 and rounded penetrating end face 308. This penetrating section 302 of FIG. 3D may be desirable in procedures where penetration of the tissue is to be performed without piercing or cutting tissue, but, rather via retracting, separating or dissecting tissue. In the embodiment of FIG. 3E, penetrating section 302' may incorporate edges 310 at the junctures of primary surfaces 304' with auxiliary surfaces 306". Edges 310 may be sharpened to facilitate piercing or cutting of tissue.

Figure 4C:
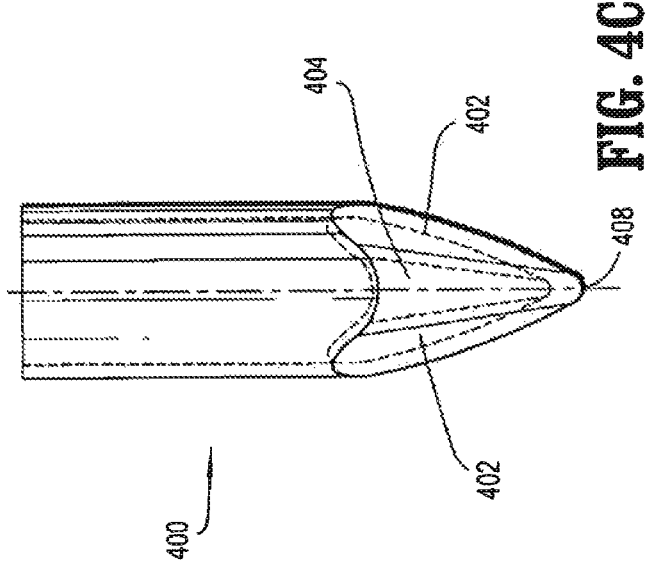
FIG. 4C is a top plan view of the optical penetrating adapter in accordance with the embodiment of FIGS. 4A-4B.
Figure 4A:
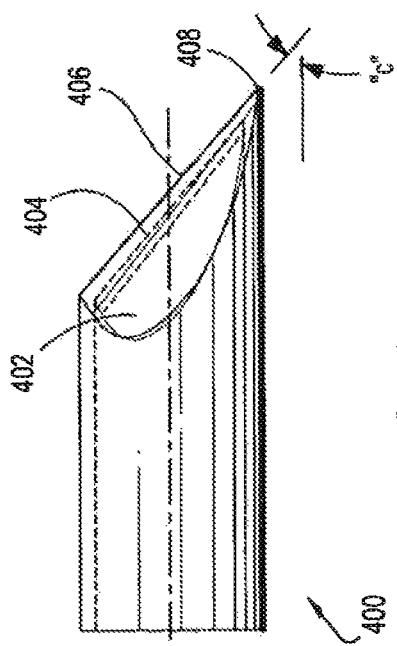
FIG. 4A is a side plan view of another alternate embodiment of the optical penetrating adapter of the present disclosure.
Figure 5A:
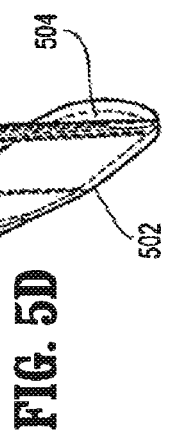
FIG. 5A is a top plan view of another alternate embodiment of the optical penetrating adapter of the present disclosure.
Figure 5B:
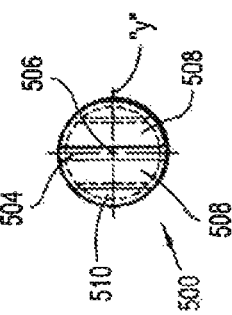
FIG. 5B is a bottom plan view of the optical penetrating adapter in accordance with the embodiment of FIG. 5A.
Figure 5C:
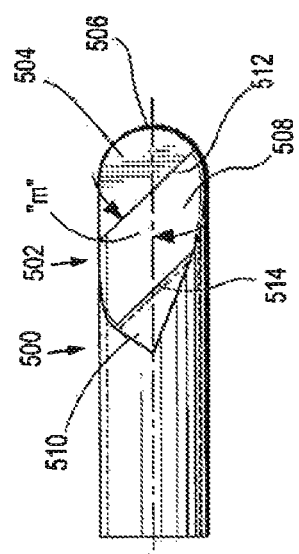
FIG. 5C is a side plan view of the optical penetrating adapter in accordance with the embodiment of FIGS. 5A-5B.
Figure 5D:
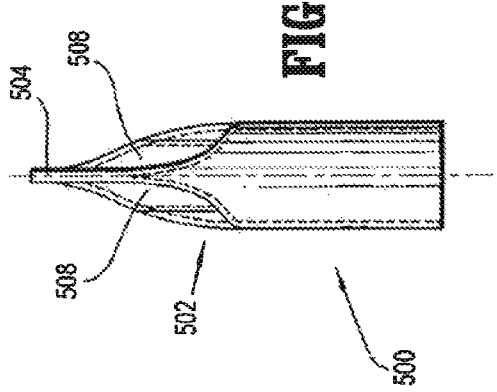
FIG. 5D is a perspective view of the optical penetrating adapter in accordance with the embodiment of FIGS. 5A-5C.
Figure 5E:
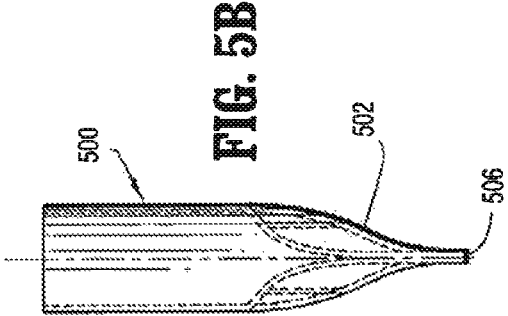
FIG. 5E is an axial view of the optical penetrating adapter in accordance with the embodiment of FIGS. 5A-5D.

FIGS. 4A-4C illustrate another alternate embodiment of the optical penetrating adapter of the present disclosure. Optical penetrating adapter 400 includes first and second primary surfaces 402 interconnected by secondary surface 404. Secondary surface 404 defines end face 406. End face 406 is arranged at an oblique angle "c" relative to adapted axis "x" and extends to penetrating tip 408. Penetrating tip 408 is radially displaced relative to the axis "x" of adapter 100 and is rounded as shown. Secondary surface 404 is preferably bulbous or generally convex and is continuous along the general axis of adapter 100 thereby permitting visualization along the axis during penetration of tissue (i.e., secondary surface 404 is devoid of any edges adjacent the axis "x" of adapter 100). Accordingly, with this embodiment of optical penetrating adapter 400, visualization along the axis "x" is not impeded. Penetrating tip 408 provides a reduced profile to facilitate initial insertion of optical penetrating adapter 400 within a narrow incision.

FIGS. 5A-5E illustrate another alternate embodiment of the optical penetrating adapter of the present disclosure. Optical penetrating adapter 500 includes penetrating section 502 defining a transparent window consisting of multiple surfaces. Specifically, penetrating section 502 includes arcuate nose 504 which defines apex or penetrating end face 506. Arcuate nose 504 is semicircular in a first extent as viewed in the side plan view of FIG. 5C and is generally rectangular in ma second extent defining a narrow cross-section as viewed in the axial view of FIG. 5E. Extending contiguously from arcuate nose 504 is a pair of opposed first surfaces 508 which are obliquely arranged relative to adapter axis "x" and diverge outwardly toward the proximal end of the adapter 500. Extending contiguously from first surfaces 508 is a pair of second surfaces 510 which also diverge outwardly from the adapter axis "x", preferably, at a greater angle of divergence than first surfaces 508. First surfaces 508 intersect arcuate nose 504 along lines of intersection 512. Second surfaces 510 intersect first surfaces 508 along lines of intersection 514. Lines of intersection 512, 514 are each obliquely arranged relative to longitudinal axis "x" at an angle "m". Angle "m" preferably ranges from about 30° to about 60°, more preferably, about 45°. First and second surfaces 508, 510 may be planar, concave, or convex in configuration. Penetrating section 502 of optical penetrating adapter 500 presents a reduced profile which facilitates passage of the penetrating section 502 through tissue. In particular, the narrow configuration of arcuate nose 504 permits relatively easy initial entry into, and manipulation within, the narrow incision or wound site. Primary and secondary surfaces 508, 510 provide gradual retraction or dissection of the tissue defining the incision or opening during passage of the optical penetrating adapter 500 through tissue. Moreover, the arrangement of primary and secondary surfaces 508, 510 and the oblique characteristic of the lines of intersection 512, 514 define a streamlined profile which substantially minimizes tissue resistance.

FIGS. 6A-6E illustrates another embodiment of the present disclosure. Optical penetrating adapter 600 is similar to the optical penetrating adapter 500 of FIGS. 5A-5E. However, with this embodiment arcuate nose 602 is generally tapered in a first extent in the side plan view of FIG. 6C, defining a frusto-conical configuration having rounded arcuate apex or end face 604. The frusto-conical configuration defines a narrow nose 602 relative to the corresponding nose 504 of optical penetrating adapter 500. This narrow nose 602 further facilitates initial entry and manipulation within a relatively small incision or opening in tissue. In addition, the gradual taper of nose 602 provides for a relatively gradual retraction or separation of tissue.

FIGS. 7A-7E illustrate another alternate embodiment of the optical penetrating adapter of the present disclosure. Optical penetrating adapter 700 includes an optical window having arcuate or bulbous penetrating surface 702 defining rounded apex or penetrating end face 704. Penetrating end face 704 is arranged at an oblique angle relative to the adapter axis "x" to define an extreme tip 704'. First surfaces 706 contiguously extend from penetrating surface 704 and are preferably substantially parallel to adapter axis "x". Second surfaces 708 intersect first surfaces 706 along lines of intersection 710 and diverge outwardly in the proximal direction at a predetermined angle relative to adapter axis "x". Third surfaces 712 intersect second surfaces 708 along lines of intersection 714 and extend outwardly relative to axis "x" at a predetermined angle greater than the angle of divergence of second surfaces 708. Optical penetrating adapter 700 provides a more narrow profile relative to the adapters of the prior embodiments. In particular, the extreme tip 704' as provided by the inclination of penetrating end face 704 permits insertion in relatively narrow incision or opening sites. The parallel arrangement of first surfaces 706 presents a reduced profile during initial passage of penetrating end 702 through tissue. The oblique arrangement of second and third surfaces 708, 712 provides for gradual separation of the tissue while the oblique lines of intersection 710, 714 present minimal resistance to the engaged tissue.

The transparent windows in accordance with this disclosure may include an image directing member (not shown) for directing optical images into the longitudinal passage 206 of the cannula sleeve 202 or back to an image apparatus. The image directing member may be a lens, an optical prism, an optical mirror, or like image directing medium.

Figure 8:
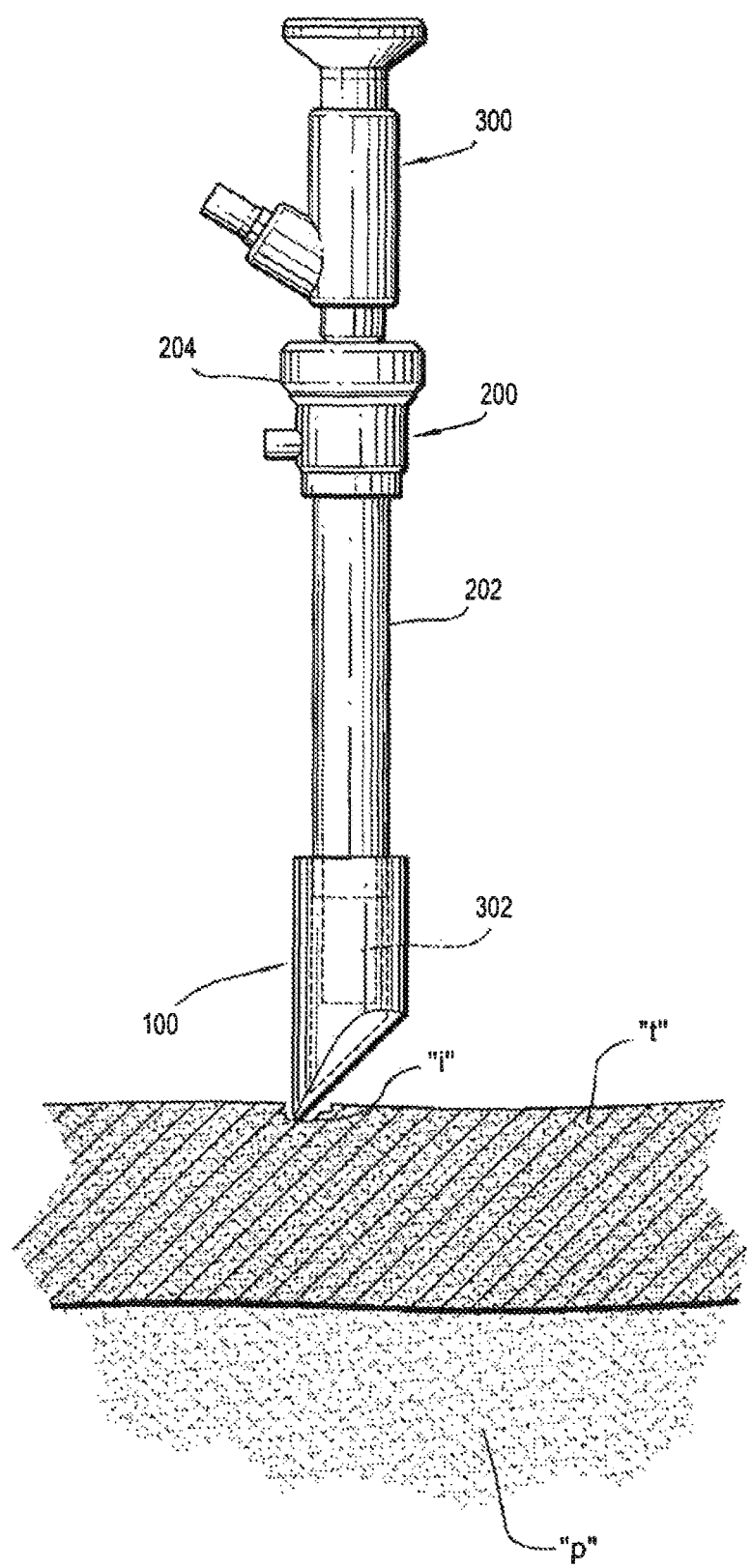
FIG. 8 is a view illustrating the optical penetrating adapter mounted to the cannula assembly and with an endoscope positioned therein to permit visualization during penetration of tissue.

Referring now to FIG. 8, the use of the optical penetrating adapters during a laparoscopic surgery will be discussed. The peritoneal cavity "p" is insufflated as is conventional to raise the cavity wall to provide greater access to tissue and organs therewithin. Thereafter, any of the aforementioned optical penetrating adapters is mounted to cannula sleeve 202 of the conventional cannula assembly 200. (For reference purposes, adapter 100 of FIG. 2A will be utilized). An endoscope 300 is positioned within the cannula assembly 200. One suitable endoscope is disclosed in commonly assigned U.S. Pat. No. 5,718,664 to Peck et al., the contents of which are incorporated herein by reference. The internal seal within cannula housing 204 may form a fluid tight seal about the endoscope 300. As appreciated, endoscope 300 is advanced within cannula sleeve 202 until the distal end 302 of the endoscope 300 is adjacent transparent window 108 of optical penetrating adapter 100. In this position, the distal lens element of the endoscope 300 is adjacent transparent window 108 so as to be capable of viewing the tissue being entered. Endoscope 300 may be secured relative to the cannula assembly 200 utilizing a resilient washer or a cam locking system incorporated with the cannula assembly 200 or formed separately therefrom.

The procedure is continued by positioning optical penetrating adapter 100 within a previously formed opening or incision "i" in tissue "t" and advancing the adapter 100 to retract, dissect, or penetrate the tissue. During penetration of the body tissue, the surgeon observes the underlying tissue through the endoscope 300 to ensure there is no undesired contact with organs, tissue, etc. lying beneath the peritoneal lining. In instances where a video system is utilized, the surgeon simply observes the penetration of body tissue "t" via any known video monitor. Once the surgeon penetrates the body tissue "t" and positions the distal end of cannula sleeve 202 in the desired position within the peritoneal cavity "p" as observed through the endoscope 200, the surgeon discontinues the application of force. Surgery is then carried out through other cannula assemblies which access the peritoneal cavity. This surgery may be monitored with endoscope 300 as visualized through transparent window 108.

It will be understood that various modifications can be made to the embodiments of the present invention herein disclosed without departing from the spirit and scope thereof. For example, the present disclosure also contemplates a surgical kit which incorporates at least one, and preferably, at least two, of the aforedescribed optical penetrating adapters with or without a cannula assembly. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. An optical penetrating system for permitting visualization comprising:
    a cannula sleeve including an internal longitudinal passage dimensioned to permit passage of surgical instrumentation; and
    an adapter member adapted for mounting directly to a distal end of the cannula sleeve, the adapter member defining a central longitudinal axis, and including an optical window with a distal end defining a penetrating surface configured to facilitate advancement of the adapter member through tissue, the optical window including a pair of first surfaces extending proximally and contiguously from the penetrating surface and in a parallel relation to the central longitudinal axis, a pair of second surfaces intersecting the pair of first surfaces, and extending proximally and contiguously therefrom, and a pair of third surfaces intersecting the pair of second surfaces, and extending proximally and contiguously therefrom, the penetrating surface of the optical window being arcuate in configuration and defining a rounded penetrating end face, the end face of the penetrating surface being offset from the central longitudinal axis of the adapter member.

2. The optical penetrating system of claim 1, wherein the pair of second surfaces intersect the pair of first surfaces along first lines of intersection forming a first oblique angle with the central longitudinal axis of the adapter member.

3. The optical penetrating system of claim 2, wherein the pair of third surfaces intersect the pair of second surfaces along second lines of intersection forming a second oblique angle with the central longitudinal axis of the adapter member.

4. The optical penetrating system of claim 1, wherein the pair of second surfaces diverge outwardly in a proximal direction relative to the central longitudinal axis of the adapter member to define a first angle.

5. An adapter member configured and dimensioned for use with a cannula sleeve including an internal longitudinal passage dimensioned to permit passage of surgical instrumentation, the adapter member defining a central longitudinal axis and comprising:
    a mounting section configured for direct connection to a distal end of the cannula sleeve; and
    a penetrating section positioned distally of the mounting section, the penetrating section including an optical window with a distal end defining a penetrating surface configured to facilitate advancement of the adapter member through tissue, the optical window including a pair of first surfaces extending proximally and contiguously from the penetrating surface and in a parallel relation to the central longitudinal axis, a pair of second surfaces intersecting the pair of first surfaces, and extending proximally and contiguously therefrom, and a pair of third surfaces intersecting the pair of second surfaces, and extending proximally and contiguously therefrom, the penetrating surface of the optical window being arcuate in configuration and defining a rounded penetrating end face offset from a central longitudinal axis of the adapter member.

6. The adapter member of claim 5, wherein the mounting section is cylindrical in configuration.

7. The adapter member of claim 6, wherein the mounting section defines an internal bore configured to receive a portion of the cannula sleeve.

8. The adapter member of claim 7, wherein the internal bore is dimensioned to receive the portion of the cannula sleeve in frictional relation.

9. The adapter member of claim 6, wherein the mounting section is configured for insertion into a portion of the cannula sleeve.

10. The adapter member of claim 9, wherein the mounting section is dimensioned for receipt within the portion of the cannula sleeve in frictional relation.

11. The adapter member of claim 5, wherein the pair of second surfaces intersect the pair of first surfaces along first lines of intersection forming a first oblique angle with a central longitudinal axis of the adapter member.

12. The adapter member of claim 11, wherein the pair of third surfaces intersect the pair of second surfaces along second lines of intersection forming a second oblique angle with the central longitudinal axis of the adapter member.

13. The adapter member of claim 5, wherein the pair of second surfaces diverge outwardly in a proximal direction relative to a central longitudinal axis of the adapter member to define a first angle.

14. An optical penetrating system for permitting visualization comprising:
    a cannula sleeve including an internal longitudinal passage dimensioned to permit passage of surgical instrumentation; and
    an adapter member adapted for mounting directly to a distal end of the cannula sleeve, the adapter member defining a central longitudinal axis, and including an optical window with a distal end defining a penetrating surface configured to facilitate advancement of the adapter member through tissue, the optical window including a pair of first surfaces extending proximally and contiguously from the penetrating surface and in a parallel relation to the central longitudinal axis, a pair of second surfaces intersecting the pair of first surfaces, and extending proximally and contiguously therefrom, and a pair of third surfaces intersecting the pair of second surfaces, and extending proximally and contiguously therefrom, the pair of second surfaces diverging outwardly in a proximal direction relative to the central longitudinal axis of the adapter member to define a first angle, the pair of third surfaces diverging outwardly in a proximal direction relative to the central longitudinal axis of the adapter member to define a second angle greater than the first angle.

15. An adapter member configured and dimensioned for use with a cannula sleeve including an internal longitudinal passage dimensioned to permit passage of surgical instrumentation, the adapter member defining a central longitudinal axis and comprising:
    a mounting section configured for direct connection to a distal end of the cannula sleeve; and
    a penetrating section positioned distally of the mounting section, the penetrating section including an optical window with a distal end defining a penetrating surface configured to facilitate advancement of the adapter member through tissue, the optical window including a pair of first surfaces extending proximally and contiguously from the penetrating surface and in a parallel relation to the central longitudinal axis, a pair of second surfaces intersecting the pair of first surfaces, and extending proximally and contiguously therefrom, and a pair of third surfaces intersecting the pair of second surfaces, and extending proximally and contiguously therefrom, the pair of second surfaces diverging outwardly in a proximal direction relative to the central longitudinal axis of the adapter member to define a first angle, the pair of third surfaces diverging outwardly in a proximal direction relative to the central longitudinal axis of the adapter member to define a second angle greater than the first angle.

* * * * *